United States Patent [19]

Tessitore

[11] Patent Number: 4,554,278

[45] Date of Patent: Nov. 19, 1985

[54] HYDROXYBENZENESULFONIC ACID SALTS OF 5-(O-CHLOROBENZYL)-4,5,6,7-TETRAHYDROTHIENE [3,2-C] PYRIDINE USEFUL IN INHIBITING BLOOD-PLATELET AGGREGATION

[76] Inventor: Pietro T. Tessitore, Via Dante Alighieri, 71, 18038 Sanremo, Italy

[21] Appl. No.: 517,916

[22] Filed: Jul. 28, 1983

[30] Foreign Application Priority Data

Jul. 28, 1982 [IT] Italy .................................. 22600 A/82

[51] Int. Cl.$^4$ ...................... A61K 31/44; C07D 471/04
[52] U.S. Cl. ..................................... 514/301; 546/114
[58] Field of Search ........................ 546/114; 424/256; 514/301

[56] References Cited

U.S. PATENT DOCUMENTS 4,051,141  9/1977  Castaigne .......................... 546/114

FOREIGN PATENT DOCUMENTS 2000767  1/1979  United Kingdom .

OTHER PUBLICATIONS

Hauke et al., Chem. Abstracts, vol. 94, 191931 (1981).
Sin et al., Chem. Abstracts, vol. 95, 73623 (1981).

*Primary Examiner*—Henry R. Jiles
*Assistant Examiner*—Bernard L. Dentz
*Attorney, Agent, or Firm*—Stevens, Davis, Miller & Mosher

[57] ABSTRACT

The invention relates to new hydroxybenzenesulfonic acid salts of 5-(o-chlorobenzyl)-4,5,6,7-tetrahydrothieno [3,2-c] pyridine, to the preparation method thereof and to the pharmaceutical compositions containing them.

The new hydroxybenzenesulfonic acid salts of 5-(o-chlorobenzyl)-4,5,6,7-tetrahydrothieno [3,2-c] pyridine are endowed with platelet aggregation inhibiting activity, with angioprotective activity and with normalizing activity of the blood lipids balance.

4 Claims, No Drawings

HYDROXYBENZENESULFONIC ACID SALTS OF 5-(O-CHLOROBENZYL)-4,5,6,7-TETRAHYDRO-THIENE [3,2-C] PYRIDINE USEFUL IN INHIBITING BLOOD-PLATELET AGGREGATION

This invention relates to new hydroxybenzenesulfonic acid salts of 5-(o-chlorobenzyl)-4,5,6,7-tetrahydrothieno[3,2-c]pyridine, to the method for the preparation thereof and to the pharmaceutical composition containing them. The new compounds of the present invention are endowed with platelet aggregation inhibiting activity, with angioprotective activity and with normalizing activity of the blood lipids balance.

The compounds of this invention may be represented by the general formula (I)

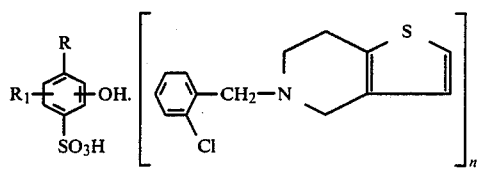

wherein R is H, or OH or $SO_3H$; $R_1$ is H or OH, provided that when R=OH, $R_1$ is always H; n is 1 or 2.

5-(o-chlorobenzyl)-4,5,6,7-tetrahydrothieno[3,2-c]pyridine (which hereinbelow will be indicated for brevity as ticlopidine) is, as known, a platelet aggregation inhibitor; its mechanism of action consists in an overproduction, at the platelet level, of cAMP, of antithrombotic prostaglandins ($PGE_1$ and $PGE_2$) and prostacyclins ($PGI_2$). Furthermore, ticlopidine inhibits fibronectine with subsequent antagonism of platelet aggregation and adhesiveness. A further property of ticlopidine is its action on erythrocytes with subsequent decrease of the viscous properties of red cells. The angioprotective activity of some hydroxybenzene sulfonic acids is well known. These acids act selectively on the arterio-venous capillaries thus normalizing their resistance and permeability; moreover, they are endowed with anti-haemorragic and anti-exudation activity. For these drugs a normalizing activity in the essential dislipidaemia has been proven.

The Applicant has now found that by salifying ticlopidine with some hydroxybenzenesulfonic acids, there are obtained compounds showing a more complete therapeutical activity, a toxicity lower than that of the starting compounds and a poorer induction of side-effects. Moreover, the therapeutic activity is longer acting because of the slow release of the single components after the administration.

The amount of the drug able to induce a significative platelet aggregation inhibition, as shown by preliminary tests on rats in lower than the amount of ticlopidine necessary to reach an equally in tense effect. This fact results in a remarkable reduction of the undesired effects and expecially results in a reduction of the bleeding time.

The compounds of this invention have been tested in order to characterize them from the pharmacological point of view.

In particular, and only as example, the Applicant will refer the results when using the salt obtained by salifying 2,5-dihydroxybenzenesulfonic acid with ticlopidine (the salification product will be indicated hereinbelow for brevity as C-1).

EFFECTS ON THE ADP INDUCED PLATELET AGGREGATION

SINGLE ADMINISTRATION OF THE DRUGS

The results obtained after single administration of C-1 or of ticlopidine-HCl, expressed as effect on the ADP induced platelet aggregation, in vitro, are summarized in the following Table 1. The effect of both drugs is apparent for all the used doses: Dunnet's test is always significative.

TABLE 1

Effect of the single administration of C-1 and ticlopidine-HCl on the ADP induced platelet aggregation. (For the tests Wistar rats have been used of 240 g body weight)

| | | PEAK OF THE CURVE (mm) | | | |
|---|---|---|---|---|---|
| | | ORIGINAL SCALE | | LOGARITHMIC SCALE | |
| DOSE** | RATS (No.) | MEAN | STAT. DEV. | MEAN | STAT. DEV.* |
| Controls | | | | | |
| — | 5 | 22.38 | 4.51 | 1.343(&) | 0.088 |
| C-1 | | | | | |
| 25 (16.7) | 5 | 14.22 | 1.94 | 1.150 | 0.059 |
| 50 (33.3) | 5 | 10.18 | 3.69 | 0.983 | 0.166 |
| 100 (66.7) | 5 | 7.94 | 1.47 | 0.894 | 0.080 |
| Ticlopidine-HCl | | | | | |
| 25 | 5 | 11.64 | 2.30 | 1.059 | 0.086 |
| 50 | 5 | 8.52 | 1.66 | 0.924 | 0.085 |
| 100 | 5 | 5.20 | 0.95 | 0.710 | 0.080 |

Remarks:
**Numbers in ( ) indicate the corresponding mg of ticlopidine-HCl
*STAT. DEV. = Statistical Deviation
(&)All the 6 groups treated differ significatively or very significatively from controls (Dunnet's test)

REPEATED ADMINISTRATION OF THE DRUGS

The results obtained after repeated administration of C-1 or of ticlopidine-HCl expressed as effect on the ADP induced platelet aggregation in vitro are summarized in Table 2. The effect of both drugs is apparent for all the doses used in the test: Dunnet's test is always highly significative.

For equal doses of ticlopidine-HCl and of C-1, the anti-aggregation activity of C-1 is significatively higher than that of ticlopidine-HCl, the power ratio being 4.91 and the pertinent confidence limits (at 95%) being 2.96 and 11.18.

TABLE 2

Effect of the repeated administration of C-1 and ticlopidine-HCl on the ADP induced platelet aggregation (10 μM) For the tests Wistar rats have been used of about 240 g body weight.

| | | PEAK OF THE CURVE (mm) | | | |
|---|---|---|---|---|---|
| | | ORIGINAL SCALE | | LOGARITHMIC SCALE | |
| DOSE** | RATS (No.) | MEAN | STAT. DEV. | MEAN | STAT. DEV.* |
| Controls | | | | | |
| — | 5 | 29.18 | 5.89 | 1.458(&) | 0.087 |
| C-1 | | | | | |
| 10 (6.7) | 5 | 10.51 | 2.88 | 1.010 | 0.112 |
| 25 (16.7) | 5 | 8.45 | 1.03 | 0.924 | 0.054 |
| 50 (33.3) | 5 | 7.42 | 1.32 | 0.865 | 0.078 |
| Ticlopidine-HCl | | | | | |
| 10.0 | 5 | 15.60 | 2.41 | 1.89 | 0.067 |

TABLE 2-continued

Effect of the repeated administration of C-1 and ticlopidine-HCl on the ADP induced platelet aggregation (10 μM) For the tests Wistar rats have been used of about 240 g body weight.

| DOSE** | RATS (No.) | PEAK OF THE CURVE (mm) | | | |
|---|---|---|---|---|---|
| | | ORIGINAL SCALE | | LOGARITHMIC SCALE | |
| | | MEAN | STAT. DEV. | MEAN | STAT. DEV.* |
| 25.0 | 5 | 13.22 | 1.90 | 1.117 | 0.065 |
| 50.0 | 5 | 8.60 | 1.28 | 0.931 | 0.066 |

Remarks:
**Numbers in ( ) indicate the corresponding mg of ticlopidine-HCl
*STAT. DEV. = Statistical Deviation
(&)All the 6 groups treated differ very significantly from controls (Dunnet's test).

EFFECT ON THE COLLAGEN INDUCED PLATELET AGGREGATION

Compound C-1 causes an inhibition significantly higher than that caused by equal doses of ticlopidine-HCl when tested by the method of the collagen induced platelet aggregation. The results are summarized in Table 3.

TABLE 3

Effect of the single administration of C-1 and ticlopidine-HCl on the collagen induced platelet aggregation. Values obtained after collagen induction.

| DOSE** | RATS (No.) | PLATELETS NUMBER (1,000/mm³) | | | |
|---|---|---|---|---|---|
| | | ORIGINAL SCALE | | LOGARITHMIC SCALE | |
| | | MEAN | STAT. DEV.* | MEAN | STAT. DEV. |
| Controls | | | | | |
| — | 5 | 94.5 | 11.6 | 1.973(&) | 0.054 |
| C-1 | | | | | |
| 25 (16.7) | 5 | 103.4 | 15.2 | 2.011 | 0.065 |
| 50 (33.3) | 5 | 134.8 | 7.9 | 2.129 | 0.025 |
| 100 (66.7) | 5 | 204.8 | 7.3 | 2.311 | 0.016 |
| Ticlopidine-HCl | | | | | |
| 25.0 | 5 | 123.0 | 18.9 | 2.086 | 0.067 |
| 50.0 | 5 | 169.5 | 13.7 | 2.228 | 0.035 |
| 100.0 | 5 | 258.2 | 20.4 | 2.411 | 0.035 |

Remarks:
**The numbers in ( ) indicate the corresponding mg of ticlopidine-HCl
*STAT. DEV. = Statistical Deviation
(&)All the groups treated differ significantly from the controls (Dunnet's test), with the exception of the group treated with 25.0 mg/kg of C-1 (16.7 mg/kg of ticlopidine-HCl)

PROTECTIVE EFFECT ON THE INDUCED PULMONARY THROMBOSIS 3 biological tests have been carried out in order to evaluate the doses of C-1 and ticlopidine-HCl necessary to protect from pulmonary thrombosis 50% of Wistar rats ($PD_{50}$) treated with ADP (400 mg/kg i.v.; after administration of the drugs) and with collagen (0.1 ml/10 mg i.v.; 1 h and 3 hours after the administration of the drugs). (Tables 4,5 and 6).

TABLE 4

Effect of C-1 and of ticlopidine-HCl on the ADP induced pulmonary thrombosis

| DOSE* (mg/kg) | Rats tested | Rats dead | Mortality (%) | $PD_{50}$ mg/kg |
|---|---|---|---|---|
| Controls | | | | |
| — | 10 | 10 | 100 | |
| C-1 | | | | |

TABLE 4-continued

Effect of C-1 and of ticlopidine-HCl on the ADP induced pulmonary thrombosis

| DOSE* (mg/kg) | Rats tested | Rats dead | Mortality (%) | $PD_{50}$ mg/kg |
|---|---|---|---|---|
| 25 (16.7) | 10 | 8 | 80 | |
| 50 (33.3) | 10 | 7 | 70 | 53.1*** |
| 100 (66.7) | 10 | 4 | 40 | (26.2–107.7)** |
| Ticlopidine-HCl | | | | |
| 25.0 | 10 | 9 | 90 | |
| 50.0 | 10 | 5 | 50 | 59.5*** |
| 100.0 | 10 | 3 | 30 | (39.4–89.91) |

Remarks:
*the numbers in ( ) indicate the corresponding mg of ticlopidine-HCl
***the values are expressed as ticlopidine-HCl
**confidence limits at 95%

TABLE 5

Effect of C-1 and of ticlopidine-HCl on the collagen induced pulmonary thrombosis (administration after 1 h)

| DOSE** | RATS TESTED | RATS DEAD | MORTALITY % | $PD_{50}$ mg/kg |
|---|---|---|---|---|
| Controls | | | | |
| — | 10 | 9 | 90 | |
| C-1 | | | | |
| 25 (16.7) | 10 | 9 | 90 | |
| 50 (33.3) | 10 | 5 | 50 | 33.3*** |
| 100 (66.7) | 10 | 1 | 10 | (24.7–44.9)* |
| Ticlopidine HCl | | | | |
| 25.0 | 10 | 7 | 70 | |
| 50.0 | 10 | 4 | 40 | 40.9*** |
| 100.0 | 10 | 2 | 20 | (24.7–67.9)* |

Remarks:
**The numbers in ( ) indicate the corresponding mg of ticlopidine-HCl
***The values are expressed as ticlopidine-HCl
*Confidence limits (at 95%)

TABLE 6

Effect of C-1 and of ticlopidine-HCl on the collagen induced pulmonary thrombosis (administration after 3 hours)

| DOSE** | RATS TESTED | RATS DEAD | MORTALITY % | $PD_{50}$ mg/kg |
|---|---|---|---|---|
| Controls | | | | |
| — | 10 | 10 | 100 | |
| C-1 | | | | |
| 25 (16.7) | 10 | 9 | 90 | |
| 50 (33.3) | 10 | 6 | 60 | 43.1*** |
| 100 (66.7) | 10 | 3 | 30 | (28.6–65.0)* |
| Ticlopidine-HCl | | | | |
| 25.0 | 10 | 10 | 100 | |
| 50.0 | 10 | 8 | 80 | 71.3*** |
| 100.0 | 10 | 2 | 20 | (55–92.5)* |

Remarks:
**The numbers in ( ) indicate the corresponding mg of ticlopidine-HCl
***The values are expressed as ticlopidine-HCl
*Confidence limits (at 95%)

Tables 4 and 5 indicate that for those tests the $PD_{50}$ are about equivalent for C-1 and ticlopidine-HCl.

On the contrary, Table 6 shows that C-1 resulted significantly more active in protecting the animals treated from collagen induced pulmonary thrombosis, the power ratio being 1.6 $LD_{50}$ of C-1 both in rat and in mouse, after administration of the drug by oral route, is higher than 3,000 mg/kg.

In order to test subacute toxicity of C-1, Wistar rats were administered daily p.o., for 6 weeks, with the following doses of C-1: 107.5 mg/kg/day; 215.0 mg/kg/day; 430.0 mg/kg/day.

Hematochemical, hematological and histopathological tests carried out at the end of the treatment did not show any damage caused by the treatment, which did not provoke any mortality.

The preparation of the compounds of this invention is carried out by allowing a ticlopidine salt to react with an alkaline or earth-alkaline salt of the selected hydroxybenzenesulfonic acid, in a solvent, in equimolar ratio.

The hydroxybenzenesulfonic acids to be used in this invention can be selected from the group comprising 2,5-dihydroxybenzenesulfonic acid and 2,5-dihydroxybenzene-1,4-disulfonic acid.

The solvents can be selected from lower aliphatic alcohols, such as for instance methanol, ethanol, propanol; ketones or mixtures thereof.

This invention relates also to the pharmaceutical compositions containing as active ingredient one of the compounds comprised in the general formula (I).

The pharmaceutical compositions may contain the active ingredient together with organic or inorganic, liquid or solid pharmaceutically acceptable carriers and may be suitable for oral and topic administration.

The pharamaceutical preparations may be solid, such as tablets, capsules, granulates, suppositories, or liquid such as syrups.

The daily dose is comprised between 0.1 and 20 mg/kg.

The following examples are given to illustrate the present invention without limiting it in any way.

EXAMPLE 1

The solution of 6.75 g of the calcium salt of 2,5-dihydroxybenzene sulfonic acid in 12 ml of water is added dropwise into a stirred solution of 9.39 g of ticlopidine sulfate in 120 ml of anhydrous ethyl alcohol, by keeping the whole at room temperature.

After having added further 120 ml of anhydrous ethyl alcohol, the mixture is stirred for 1 h, and then is filtered and washed several times with anhydrous ethyl alcohol.

The filtered solution is concentrated under vacuum in a rotating evaporator up to about 50 ml and thereafter it is again diluted with anhydrous ethyl alcohol and concentrated to 50 ml.

After crystallization on ice, the obtained crystalline product is filtered, washed twice with anhydrous ethyl alcohol and finally is dried under vacuum at 40°–45° C.

9.5 g of 2,5-dihydroxybenzenesulfonic acid salt of 5-(o-chlorobenzyl)-4,5,6,7-tetrahydrothieno[3,2-c]pyridine are obtained.

m.p. 164°–167° C.

The elemental analysis for $C_{20}H_{20}ClNO_5S_2$ gave the following result

|  | C | H | Cl | N | S |
|---|---|---|---|---|---|
| Calculated (%) | 52.93 | 4.41 | 7.83 | 3.09 | 14.11 |
| Found (%) | 53.31 | 4.42 | 7.79 | 3.08 | 14.04 |

NMR (DMSO—$d_6$ and DMSO—$d_6$ + $D_2O$)

3.18 (t, 2H, J = 7Hz, CH₂—S);

3.66 (t, 2H, J = 7Hz, CH₂); 4.32 (2, 2H, N—CH₂—N);

4.62 (s, 2H, —CH₂—N); 6.6–8 (m, 9H aromatics)

EXAMPLE 2

The solution of 3.47 g of the potassium salt of 2,5-dihydroxybenzene-1,4-disulfonic acid in 3 ml of water is added dropwise, at room temperature, into a stirred solution of 6.25 g of ticlopidine sulfate in 100 ml of anhydrous ethyl alcohol.

By working as described in the foregoing example 1, white crystals of 2,5-dihydroxybenzene-1,4-disulfonic acid salt of 5-(o-chlorobenzyl)-4,5,6,7-tetrahydrothieno[3,2-c]pyridine (5.42 g) are obtained. m.p. 212°–214° C.

The elemental analysis for $C_{34}H_{34}Cl_2N_2O_8S_4$ gave the following result:

|  | C | H | Cl | N | S |
|---|---|---|---|---|---|
| Calculated (%) | 51.20 | 4.29 | 8.89 | 3.5 | 16.09 |
| Found (%) | 51.42 | 4.33 | 8.81 | 3.47 | 15.93 |

NMR (DMSO—$d_6$ and DMSO—$d_6$ + $D_2O$)

3.1 (t, 2H, J = 7Hz, CH₂—S);

3.6 (t, 2H, J = 7Hz, CH₂); 4.32 (s, 2H, N—CH₂—N);

4.63 (s, 2H, —CH₂—N); 6.7–7.7 (m, 8H aromatics)

We claim:

1. A hydroxybenzenesulfonic acid salt of 5-(o-chlorobenzyl)-4,5,6,7-tetrahydrothieno[3,2-c]pyridine endowed with platelet aggregation inhibiting activity, with angioprotective activity and with normalizing activity of the blood lipids balance, of the formula (I)

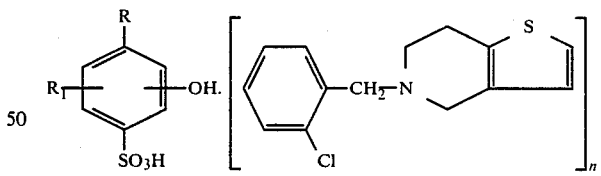

wherein R is H or OH or $SO_3H$; $R_1$ is H or OH, provided that when R=OH, $R_1$ is always H; and n is 1 or 2.

2. 2,5-Dihydroxybenzenesulfonic acid salt of 5-(o-chlorobenzyl)-4,5,6,7-tetrahydrothieno[3,2-c]pyridine.

3. 2,5-Dihydroxybenzene-1,4-disulfonic acid salt of 5-(o-chlorobenzyl)-4,5,6,7-tetrahydrothieno[3,2-c]pyridine.

4. A pharmaceutical composition having platelet aggregation inhibiting activity, angioprotective activity, and normalizing activity of the blood lipids balance, said composition having as active ingredient for the stated purposes an effective amount of a compound of the formula (I) as defined in claim 1, together with at least one pharmaceutically acceptable carrier and/or excipient.

* * * * *